US00PP15806P2

(12) United States Plant Patent
McCully

(10) Patent No.: US PP15,806 P2
(45) Date of Patent: Jun. 28, 2005

(54) ***ONCIDIUM* SWEET EARS 'THE ORCHIDWORKS'**

(50) Latin Name: *Oncidium*
Varietal Denomination: Sweet Ears The Orchid-Works

(76) Inventor: James William McCully, P.O. Box 355, Hakalau, HI (US) 96710

( * ) Notice: Subject to any disclaimer, the term of this patent is extended or adjusted under 35 U.S.C. 154(b) by 241 days.

(21) Appl. No.: 10/660,416

(22) Filed: Sep. 10, 2003

(51) Int. Cl.[7] ..... A01H 5/00
(52) U.S. Cl. ..... Plt./311
(58) Field of Search ..... Plt./311

(56) References Cited

PUBLICATIONS

Paramount Orchids, Plant Listing Oncidium Intergenerics, 1999–2000, pp. 1–7, http://www.paramountorchids.com.

*Primary Examiner*—Bruce R. Campell
*Assistant Examiner*—W C Haas

(57) ABSTRACT

A new variety of orchid plant of the genus *Oncidium,* named *Oncidium* Sweet Ears 'The OrchidWorks', distinguished particularly by a compact size, brilliant yellow and chocolate flowers with larger than typical flower segments, and self erect raceme with many branches on a typical first bloom plant.

3 Drawing Sheets

Latin name of the genus and grex of the plant claimed: The Latin name of the genus and grex of the plant claimed is *Oncidium* Sweet Ears.

Variety denomination: The present invention comprises a new and distinct cultivar of *Oncidium* orchid, and hereinafter referred to by the cultivar name *Oncidium* Sweet Ears 'The OrchidWorks'.

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

*Oncidium* comprises a genus of about 400 species from the tropical and subtropical Americas. *Oncidium* orchids are primarily epiphytic or lithophytic with a minor portion being terrestrial. All species are sympodial in growth and may vary greatly in other morphology and size.

*Oncidium* breeding is typically done from sexual methods. Asexual propagation of *Oncidium* is often done in aseptic tissue culture from apical or axillary shoots.

The new cultivar was discovered by the Inventor within the progeny of a cross made by the Inventor on Oct. 3, 1994. The Inventor selected *Oncidium* Sweet Ears 'The OrchidWorks' as a single plant from a population of over 120 plants grown by James McCully Orchid Culture Inc. dba The OrchidWorks in Hakalau, Hi., a company owned by the Inventor. *Oncidium* Sweet Ears 'The OrchidWorks' was submitted by the Inventor to a commercial tissue culture laboratory, BB Laboratory, Bangkok, Thailand, on Dec. 12, 1999, for propagation through aseptic tissue culture technique. A quantity was produced for evaluation and has demonstrated that the unique combination of characteristics as herein disclosed for the new cultivar are firmly fixed and are retained through successive generations of asexual reproduction.

Other seedlings from the cross that produced *Oncidium* Sweet Ears 'The OrchidWorks' have been commercially available from others. The characteristics of *Oncidium* Sweet Ears 'The OrchidWorks' are clearly distinguishable from the characteristics of those other plants. Those other plants were sold by The OrchidWorks without specific epithet to individuals and other nurseries. To the Inventor's knowledge, there are no named clones owned by others. Plants of the grex *Oncidium* Sweet Ears are sold as plants of the grex without specific epithet.

BRIEF SUMMARY OF THE INVENTION

The following traits have been repeatedly observed and are determined to be basic characteristics of new cultivar which in combination distinguish this *Oncidium* orchid as a new and distinct cultivar:

Flowers of the new cultivar are densely marked with chocolate bars laid over a yellow background on the sepals and petals. The labellum is bright yellow and dotted with 2 millimeter (mm) brown spots. The natural horizontal spread is 3.8 centimeters (cm); natural vertical spread is 5.1 cm; sepal width 0.8 cm; sepal length 1.5 cm; petal width 1.0 cm; petal length 1.7 cm; labellum width 3.8 cm; labellum length 3.6 cm. There are 50 to 100 flowers on a first bloom plant depending on the plant's environment.

Inflorescence is panicle, approximately 60 cm on a first bloom plant and has 5 to 7 side branches as long as 20 cm, some having secondary branching. The branches become shorter nearer the panicle apex. The panicle is self erect and does not require a stake to appropriately display the flowers. The size of the inflorescence is appropriate to the overall size of the plant and typical pot size for this cultivar.

There are generally four leaves on a mature pseudobulb, two from the apex which are larger than those produced at the base of the pseudobulb. The larger, apical leaves have been measured up to 35 cm in length with the opposing leaf being approximately 90 percent of that length. The axillary leaves at the base of the pseudobulb may be as short as to appear to be a bract and as long as 18 cm. This characteristic seems to be variable from growth to growth. The width of the larger leaves is approximately 5.5 cm. The shape is linear-ligate to lanceolate, texture and substance is subcoriaceous. The plants of *Oncidium* Sweet Ears 'The OrchidWorks' grow to maturity and flower in approximately 18 months.

Plants of the new cultivar have not been observed under all possible environmental conditions. The phenotype may vary significantly with variations in the environment such as temperature, light intensity, and day length, without however any change in genotype.

Plants of the new cultivar differ primarily from plants of the parent cultivars in flower size, panicle size, overall plant size, rate of growth, and speed to maturation. Perhaps the closest commercial comparison to the new cultivar can be made to seedling-derived *Oncidium* orchids which are genetically heterogeneous, and typically lack uniformity in growth, vigor, plant habit, and flower quality. Since this reference point has inconsistent characteristics, a direct comparison for *Oncidium* Sweet Ears 'The OrchidWorks' is not available. The new cultivar is a single genotype asexually propagated via tissue culture; thus, its combined horticultural characteristics listed above are uniform and predictable.

BRIEF DESCRIPTION OF THE DRAWINGS

The drawings show the colors of the new variety as nearly true as possible with an illustration of this type. In the drawings.

DETAILED BOTANICAL DESCRIPTION

Figure 1:
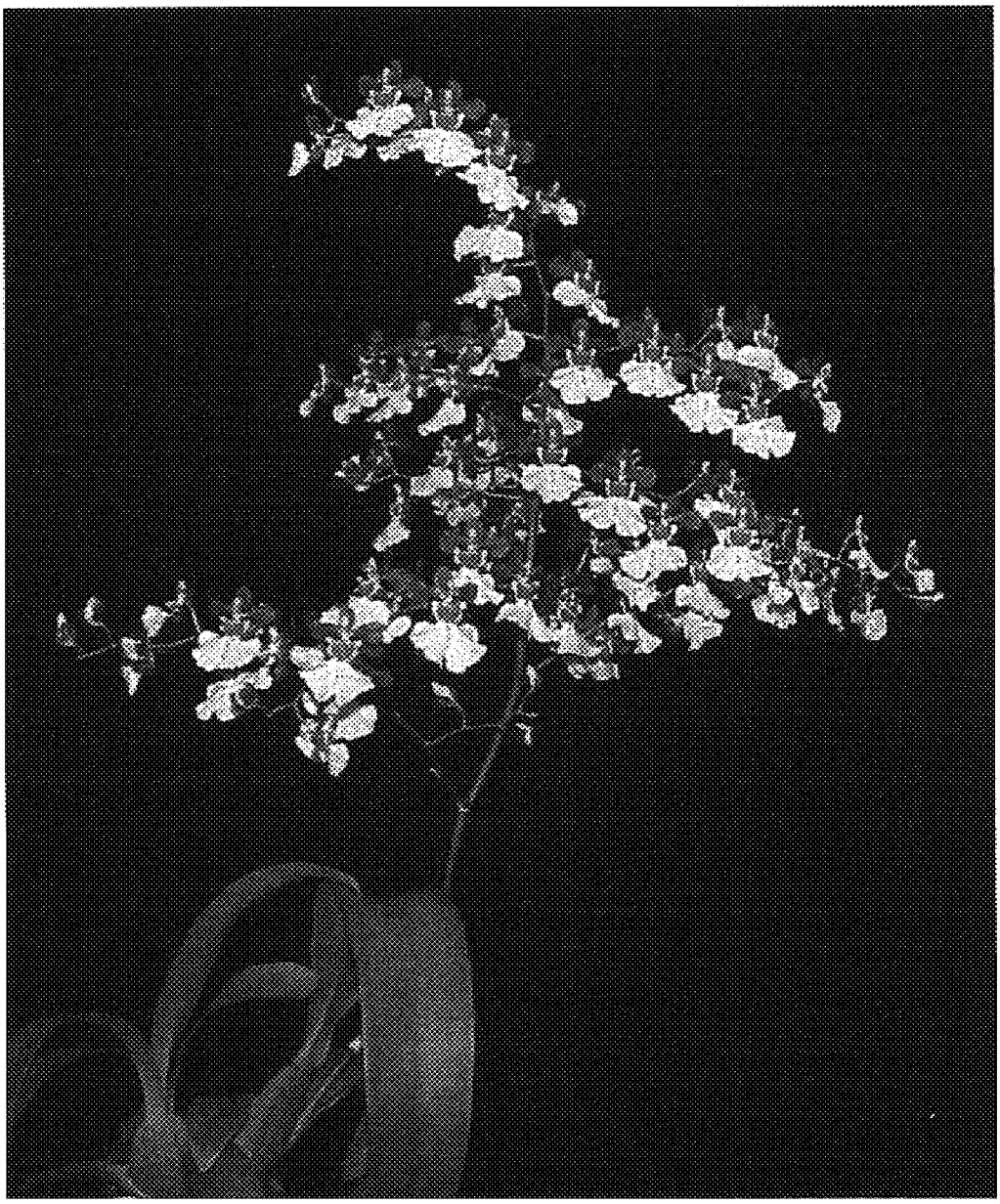
FIG. 1 is a view of the entire plant to reveal the growth habit, general characteristics with its flowers, which is typical of this new variety.
Figure 2:
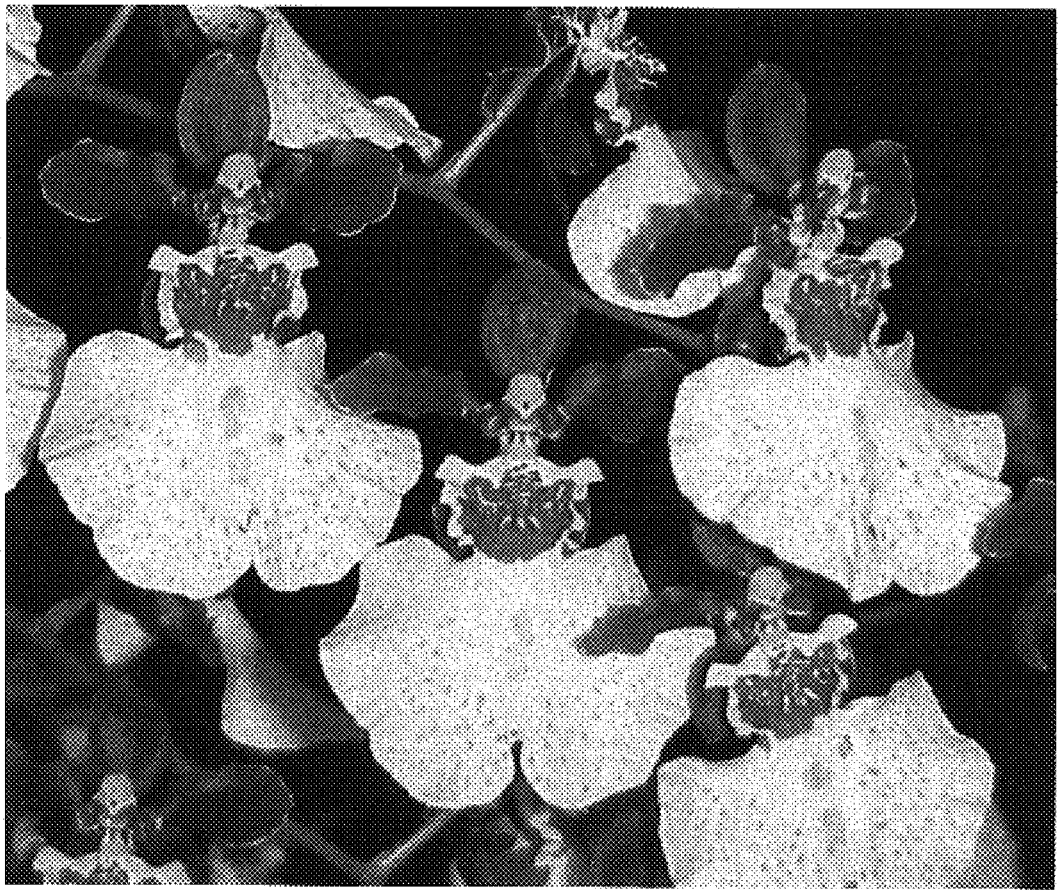
FIG. 2 is a close up view of the flowers to show their shape.
Figure 3:
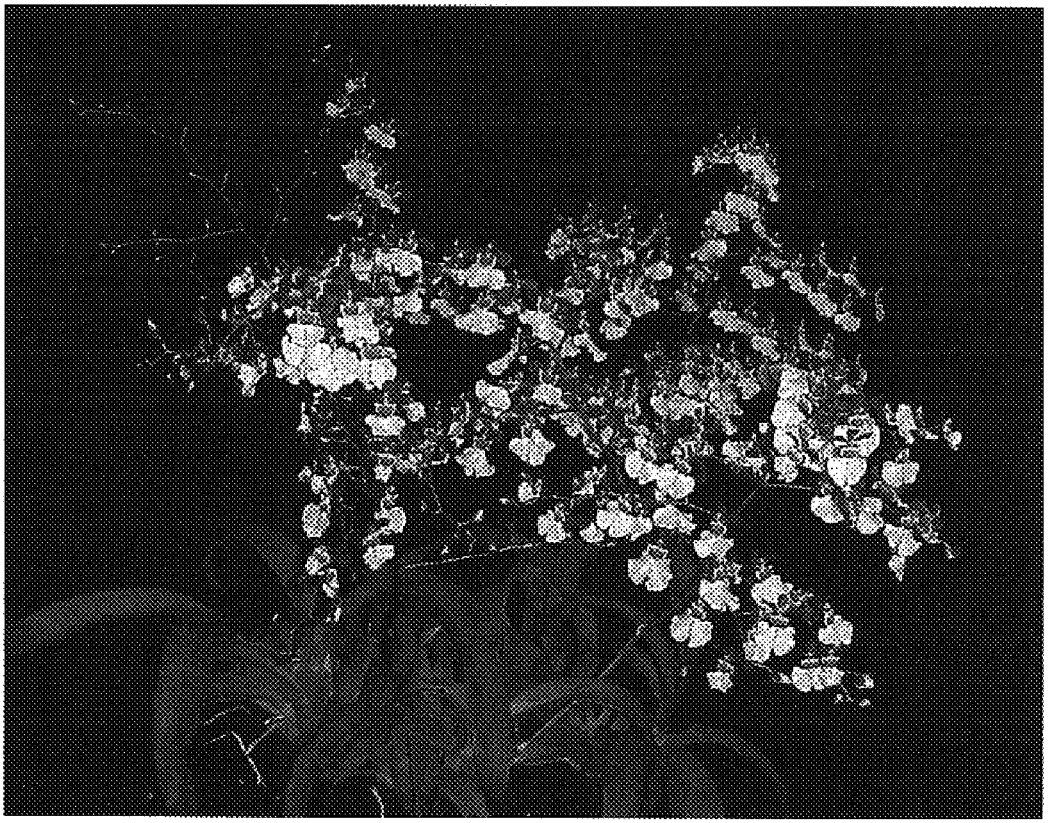
FIG. 3 is a view of several micro propagated plants.

All color references are measured against the Pantone® Color System. Colors and numerical measurements are approximate as plant growth and development depends on environmental conditions and cultural practices such as light level, temperature, water quality, fertilization formula and rate, among others, without, however, any variance in genotype.

Plants used for this description are 1 to 2 years in vivo and grown in 3.5 inch, square plastic pots, grown in a polycarbonate covered greenhouse near Hakalau, Hi., where day temperatures range from 75 to 88 degrees and night temperatures range from 62 to 75 degrees Fahrenheit. Light levels are between 1500 and 2500 foot candles. This information reflects the annual variations for the area.

Botanical classification: *Oncidium* Sweet Ears 'The OrchidWorks'.

Parentage: Seedling selected from a cross of the following:

*Seed parent.*—*Oncidium* Sweet Sugar.

*Pollen parent.*—*Oncidium* Cloud Ears.

Propagation:

*Type.*—Asexual propagation by aseptic tissue culture through axillary shoot initiation.

*Time to initiate and elongate roots in-vivo.*—About 45 days.

*Time to produce fully rooted young plant.*—About 180 days.

Root description: Thick velum covering, approximately 3 mm in diameter, white in color with the growing tip green. The exact shades of white and green vary greatly with minimal changes in environmental conditions.

Plant description: Under appropriate growing conditions, plants of the new cultivar attain a mature size of about 15 cm in height (top of leaf plane) and about 5.5 cm in width.

Foliage description:

*Arrangement.*—Sympodial growth habit.

*Quantity of leaves per growth.*—Each sympodial growth has shown four leaves, two on the apex of the pseudobulb and two from the axis at the base of the pseudobulb.

*Leaf length.*—The larger, apical leaves have been measured up to 35 cm in length with the opposing leaf being approximately 90 percent of that length. The axillary leaves at the base of the pseudobulb may be as short as to appear to be a bract and as long as 18 cm.

*Leaf width.*—The width of the larger leaves is approximately 5.5 cm.

*Leaf shape.*—The shape is linear-ligate to lanceolate, texture and substance is subcoriaceous.

*Pseudobulb shape.*—The pseudobulb shape is a laterally compressed ovoid.

*Pseudobulb length.*—The pseudobulb is approximately 7 cm long.

*Pseudobulb width.*—The pseudobulb is approximately 6 cm wide and 3.5 cm thick.

*Foliage color.*—Under the described growing conditions, the foliage color on both sides of the leaves and the pseudobulb is similar to Pantone® 576 C of the Pantone® Color System. There is no vein color distinction.

Flower/inflorescence description:

*Description.*—Panicle, approximately 60 cm on a first bloom plant and has 5 to 7 side branches as long as 20 cm, some having secondary branching. The branches become shorter nearer the panicle apex. The panicle is self erect and does not require a stake to appropriately display the flowers. The size of the inflorescence is appropriate to the overall size of the plant and typical pot size for this cultivar.

*Dimensions.*—Flower dimensions are: natural horizontal spread is 3.8 cm; natural vertical spread is 5.1 cm; sepal width is 0.8 cm; sepal length is 1.5 cm; petal width is 1.0 cm; petal length is 1.7 cm; labellum width is 3.8 cm; labellum length is 3.6 cm.

*Coloration.*—The dominant flower color appears on the labellum and is Pantone® 108C, this (yellow) is spotted with Pantone® 740C (brown); the petals are inconsistently marked with Pantone® 128C (yellow) and Pantone® 7517C (brown), brown is dominant with narrow yellow stripes laterally. The top and sides of the column are 740C (brown) changing mid column distally to 128C (yellow). The wings on the column are 740C and the bottom white. The pollinia are completely concealed by the anther cap which is 128C (yellow). If the anther cap is removed, the pollinia may be extracted and inspected showing range in color depending on age from 106C (very young flower) to 109C on flowers older than five days.

Quantity of flowers and time to flower:

*Flower longevity.*—The flowers have lasted up to 5 weeks on the plant with good environmental conditions. A first bloom plant will produce between 50 and 100 flowers, depending on environmental conditions.

*Natural flowering season.*—The natural flowering season is late summer and fall in Hawaii.

Fragrance: A faint floral scent has been identified by the Inventor.

Reproductive organs: The stamens, style and stigmas are fused into a single short structure call the column, possessing one terminal anther with pollen grains united to a pollinia, which are covered by an anther cap. The stigma is located under the column behind the pollinia. The ovary is inferior, with three carpels being present.

*Column.*—The column is erect with wings dolabriforme either side of the stigma, 0.9 cm long, 0.4 cm wide.

*Pollinia.*—Two oval masses of pollen are present, about 1 mm in diameter.

*Stigma.*—The stigma is concave, round, with a high gloss, and sticky.

*Ovary.*—The ovary is about 0.9 cm long and about 1.5 mm in diameter.

*Seed.*—Seed production has not been observed.

Disease resistance: Resistance or susceptibility to known pathogens of *Oncidiinae* has not been observed on plants grown under commercial production conditions.

General observations: Plants of *Oncidium* Sweet Ears 'The OrchidWorks' produce a pleasing arrangement of many yellow and brown flowers held on a self erect panicle. The flowers are long lasting for *Oncidiinae* and the spots on the labellum are unique. The plant grows quickly to sexual maturity.

What is claimed is:

1. A new and distinct variety of orchid plant named *Oncidium* Sweet Ears 'The OrchidWorks', substantially as illustrated and described herein.

* * * * *